(12) United States Patent
Achten et al.

(10) Patent No.: US 7,977,431 B2
(45) Date of Patent: Jul. 12, 2011

(54) DITHIOCARBAMIC ESTERS

(75) Inventors: Dirk Achten, Cologne (DE); Michael Klimpel, Pulheim-Stommeln (DE); Emilie Barriau, Mainz (DE); Lothar Reif, Dormagen (DE); Renke Mottweiler, Leverkusen (DE); Heinrich Berg, Pulheim (DE); Zsolt Szentivanyi, Leverkusen (DE); Stefan Glander, Sarnia (CA)

(73) Assignee: LANXESS Deutschland GmbH, Leverkusen (DE)

( * ) Notice: Subject to any disclaimer, the term of this patent is extended or adjusted under 35 U.S.C. 154(b) by 0 days.

(21) Appl. No.: 12/888,461

(22) Filed: Sep. 23, 2010

(65) Prior Publication Data

US 2011/0015360 A1    Jan. 20, 2011

Related U.S. Application Data

(62) Division of application No. 11/607,535, filed on Dec. 1, 2006, now Pat. No. 7,825,193, which is a division of application No. 10/662,902, filed on Sep. 15, 2003, now Pat. No. 7,169,937.

(30) Foreign Application Priority Data

Sep. 20, 2002 (DE) ................... 102 43 666

(51) Int. Cl.
*C08F 236/06* (2006.01)
*C08F 236/08* (2006.01)
*C08F 236/10* (2006.01)

(52) U.S. Cl. ...................... 525/255; 525/261
(58) Field of Classification Search .......... None
See application file for complete search history.

(56) References Cited

U.S. PATENT DOCUMENTS

| 3,839,337 A | 10/1974 | Sturm et al. |
| 6,642,318 B1 | 11/2003 | Chiefari et al. |
| 2002/0061990 A1 | 5/2002 | Charmot et al. |

FOREIGN PATENT DOCUMENTS

| DE | 2131135 A1 | 1/1972 |
| EP | 0421149 A1 | 4/1991 |
| JP | 2003-238518 | 8/2003 |
| WO | WO 9931144 A1 * | 6/1999 |

OTHER PUBLICATIONS

European Search Report cited in corresponding EP Application No. 03019662, dated Dec. 12, 2003, consisting of 6 pages.
Pongo, Laszlo et al: "On triazoles. XXXIII. The reaction of potassium triazolyldithiocarbonates with dihaloalkanes", Journal of Heterocyclic Chemistry, Bd. 31, Nr. 4, 1994, Seiten 997-1004 XP-009022975.
Abe, Tetsuya et al., "Preparation of difluoroalkenyl carbamates as pesticides", Kumiai Chemical Industry Co., Ltd., Japan, Ihara Chemical Industry, Aug. 27, 2003 XP-002264574.
Childs et al., J. Chem. Soc, 1948, Seite 2182 XP-002264572.
Sakurai et al:, Synthesis, 1978, p. 370 XP-002264573.

* cited by examiner

Primary Examiner — Yong Chu
Assistant Examiner — Michael Barker
(74) Attorney, Agent, or Firm — Michael A. Miller

(57) ABSTRACT

The present invention relates to dithiocarbamic esters, their preparation and their use for regulating the degree of polymerization during the polymerization of monomers, such as during the polymerization of chloroprene to give polychloroprene, and during the polymerization of 2,3-dichlorobutadiene to give poly-2,3-dichlorobutadiene, and during the copolymerization of chloroprene with 2,3-dichlorobutadiene. The present invention further relates to polymers which are obtainable via the polymerization of monomers in the presence of the dithiocarbamic esters of the invention. The present invention also relates to polymers which contain end groups derived from the dithiocarbamic esters of the present invention.

2 Claims, No Drawings

DITHIOCARBAMIC ESTERS

This application is a divisional of U.S. patent application Ser. No. 11/607,535 filed Dec. 1, 2006, entitled "Dithiocarbamic Esters", now pending, which is a divisional U.S. patent application Ser. No. 10/662,902 filed Sep. 15, 2003, entitled "Dithiocarbamic Esters", issued as U.S. Pat. No. 7,169,937 on Jan. 30, 2007, the contents of which are hereby incorporated by reference in their entirety.

FIELD OF THE INVENTION

The present invention relates to dithiocarbamic esters, to the preparation of dithiocarbamic esters and to the use thereof for regulating the degree of polymerization during the polymerization of monomers, such as during the polymerization of chloroprene to give polychloroprene, and during the polymerization of 2,3-dichlorobutadiene to give poly-2,3-dichlorobutadiene, and during the copolymerization of chloroprene with 2,3-dichlorobutadiene. The present invention further relates to polymers prepared by the polymerization of monomers in the presence of the dithiocarbamic esters of the present invention. The present invention also relates to polymers, which contain end groups derived from the dithiocarbamic esters of the present invention.

BACKGROUND OF THE INVENTION

WO 99/31144 discloses the use of dithiocarbamic esters for regulating the degree of polymerization during the polymerization of vinyl monomers.

DE-A 21 56 453 discloses dialkoxyxanthogen disulphides and their use as regulators during the polymerization of dienes.

The use of dithiocarboxylic esters and of xanthogenic esters for regulating the polymerization of vinyl monomers is described in WO 98/01478. WO 01/42312 discloses the use of dithiocarboxylic esters and in and WO 98/58974 discloses the use of xanthogenic esters.

WO 99/35177 and Tetrahedron Letters 1999, pp. 2435 et seq. also discuss polymerization regulators.

No process has been described for the controlled preparation of polymers based on dienes in the presence of dithiocarboxylic ester, xanthogenic ester, dithiocarbamic ester, giving industrially relevant molar masses Mn>50 000 g/mol with good yields in an acceptable time, but such a process is desirable.

Useful dithiocarboxylic esters/xanthogenic esters/dithiocarbamic esters must in principle be capable of industrial preparation with good purity and with high yield in order to be suitable for industrial use in regulating the degree of polymerization during the polymerization of vinyl monomers and diene monomers.

Processes for preparing dithiocarbamic esters are known and are described by way of example in Houben-Weyl (eds.: K. H. Bückel, J. Falbe, H. Hagemann, M. Hanack, B. Klamann, R. Kreher, H. Kropf, M. Regitz), Thieme Verlag, Stuttgart 1983, 4th edition, Volume E 4, pp. 458-478.

Dithiocarbamic esters may generally be prepared by the following process known from the literature. Dithiocarbamates are prepared by reacting amines with carbon disulphide in the presence of at least equimolar amounts of a base (e.g. potassium hydroxide) in aqueous solution, and after isolation these may be reacted with an organic halogen compound to give dithiocarbamic esters, with elimination of the salt derived from the base and the halide.

WO 99/31144 discloses the use of sodium hydride in organic solvents as a deprotonating reagent.

Dithiocarbamic esters prepared by the synthesis methods of WO 99/31144 have little suitability for industrial use, due to excessively low yields and inadequate product selectivity. The purities obtained are inadequate for industrial use of these dithiocarbamic esters as regulators (i.e. for regulating the degree of polymerization during the polymerization of monomers) unless a purification step is inserted.

The dithiocarbamic esters prepared as described in WO 99/31144 may, where appropriate, be subjected to distillation, recrystallization or chromatography to obtain products sufficiently pure to permit their use as polymerization regulators. High purity of the dithiocarbamic esters is necessary, since the (strong-smelling) by products identified by analysis, some of which are mercaptans, themselves exhibit regulating activity in the polymerization of vinyl monomers and dienes.

Distillation generates high losses, since the dithiocarbamic esters are inherently thermally unstable, and can in turn lead to the by-products mentioned. Purification via crystallization is also associated with significant yield losses, while chromatographic purification on an industrial scale is too expensive.

A process which permits the production of suitable dithiocarbamic esters from inexpensive starting chemicals at good purity would therefore represent a significant technical advance.

The purity of the dithiocarbamic esters prepared by the process of the patent was determined not only by testing for the customary physical data but also by testing their suitability as molecular weight regulators during the emulsion polymerization of chloroprene. For this, chloroprene was polymerized in a standardized process with addition of controlled amounts of dithiocarbamic ester. The resultant elastomer (polychloroprene) was worked up. The solution viscosity of the resultant product was determined from the solid (5% strength solution in toluene) or latex (8.6% strength solution in toluene) with the aid of a Brookfield viscometer at 20° C. The molecular weight Mn (the average molar mass) was determined by means of GPC (gel permeation chromatography), using polystyrene calibration as reference. Chloroprene, which can be polymerized to give polychloroprene, has the following structure:

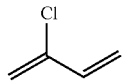

Familiar regulators for the polymerization of chloroprene, e.g. dodecyl mercaptan or xanthogen disulphides, give products with only modest control of molecular weight. The molecular weights obtained (for example determined using the Mooney viscosity to ISO 289 with no pretreatment) depend on the amount of regulator used, the particle size, the diffusion of the regulator, and also the number of active chains in a micelle in the case of emulsion polymerization. Adjustment of molecular weight via the conversion is not possible here.

The preparation of polychloroprene from chloroprene is known. It is usually carried out as an emulsion polymerization. The emulsion polymerization process proceeds in two stages, the polymerization to give the latex being carried out in the first stage, and the work-up of the latex to give the finished rubber being carried out in the second stage, for example by freeze coagulation. The process requires a product molecular weight of >20 Mooney units (see ISO 289) in order to ensure processability in the above-mentioned process. This corresponds approximately to a number-average molar mass (Mn) of about >100,000 g/mol by GPC (polystyrene calibration).

An object of the present invention is therefore to provide a compound which is suitable for regulating the molecular weight during the polymerization of one or more different monomers, at least one monomer containing a diene group.

Another object of the present invention is to provide a process for preparing this compound, and also to provide a process for polymerizing monomers in the presence of this compound.

Another object of the present invention is to provide polymers, which are prepared by polymerization in the presence of the compound mentioned.

SUMMARY OF THE INVENTION

The present invention relates to a compound of the formula (I)

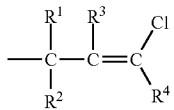

where
R is a halogen-substituted alkenyl radical, preferably a radical of the formula

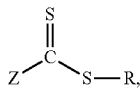

where $R^1$, $R^2$, $R^3$ and $R^4$, independently of one another, are H or $C_1$-alkyl to $C_4$-alkyl, the cis form and the trans form being equally preferred, and 3-chloro-2-butenyl being more preferred,
and where
Z is either a substituted or unsubstituted heterocyclic radical which contains at least one nitrogen atom and which has linkage at one nitrogen atom to the $-CS_2-R$ group of formula (I) and which, in the parent form in which there is a hydrogen atom bonded to the nitrogen atom which has linkage to the $-CS_2R$ group of formula (I), has a $pK_a$ value in the range from 12 to 20, preferably from 14 to 18,
or where
Z is a radical of the formula (II),

where
A and B have been selected independently of one another from the group consisting of hydrogen, substituted or unsubstituted alkyl, substituted or unsubstituted alkenyl, substituted or unsubstituted alkoxy, substituted or unsubstituted acyl, substituted or unsubstituted aroyl, substituted or unsubstituted aryl, substituted or unsubstituted heteroaryl, substituted or unsubstituted alkylsulphonyl, substituted or unsubstituted alkylsuiphinyl, substituted or unsubstituted alkylphosphonyl, substituted or unsubstituted arylsulphinyl and substituted or unsubstituted arylphosphonyl, preferably unsubstituted heteroaryl, more preferably pyrrole or imidazole.

and where the $pK_a$ value of the protonated form of formula (III)

is in the range from 12 to 20, preferably from 14 to 18.

Most preferably, Z is pyrrole ($pK_a$ value=17), imidazole ($pK_a$ value=14.5), pyrazole ($pK_a$ value=14.0), indole ($pK_a$ value=17), carbazole ($pK_a$ value=17), N-(methyl/ethyl)acetamide ($pK_a$ value=16.6), N-phenylacetamide ($pK_a$ value=16.6), 2-piperidinone ($pK_a$ value=16.6), 2-azepanone ($pK_a$ value=16.6) or 2-azocanone ($pK_a$ value=16.6).

The present invention also relates to a process for preparing the compound of the formula (I) including
a) providing a compound of the formula (IV),

where Z is as defined and M is an alkali metal, preferably potassium,
b) reacting this compound with a compound of the formula (V)

where R is as defined for formula (I) and X is Cl, Br or I, preferably Cl or Br.

The present invention also provides the use of the compound of the formula (I) for regulating the degree of polymerization during the polymerization of monomers.

The present invention also provides a process for preparing a polymer by polymerizing monomers in the presence of the compound of the formula (I).

According to the present invention one monomer, two or more different monomers may be polymerized. If two or more different monomers are polymerized the term copolymerization is used.

According to the present invention preferably all of the monomers contain either a vinyl group or a diene group, and more preferably at least one monomer containing a diene group. Most preferably, one monomer is chloroprene and/or 2,3-dichlorobutadiene.

According to the present invention the process can be carried out to prepare a polymer in emulsion (known as emulsion polymerization).

The present invention also provides a polymer obtainable by this process.

The present invention also provides a polymer which contains end groups of the formula (VI)

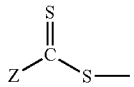
(VI)

and end groups of the formula (VIa)

R—  (VIa), where Z and R are as defined above for formula (I).

Preferably, the polymer contains repeat units derived from a monomer which contains diene groups, more preferably derived from chloroprene and/or 2,3-dichlorobutadiene. Also, according to the present invention, the polymer can also contain repeat units derived from one, two or more different, monomers containing a vinyl group or diene group.

One of the advantages of the present invention is a compound which is suitable for regulating the molecular weight during the polymerization of monomers, where at least one monomer or all contain a diene group, (preferably chloroprene), and where there is a dependent relationship between the molecular weight and the amount of regulator, and also the conversion of the monomer.

Another advantage of the present invention is the provision of an efficient process, capable of implementation on an industrial scale, for preparation of this compound in pure form.

Another advantage of the present invention is the provision of a novel process, improved over familiar emulsion polymerization processes, for the polymerization of monomers, where at least one monomer or all contain a diene group, (preferably chloroprene). The process of the present invention features improved control of molecular weight and molecular weight distribution with no sacrifice of polymerization rate, and therefore gives higher throughput rates than conventional processes, and fewer production problems, while product quality is higher.

Another advantage of the present invention is polymers which are obtainable through polymerization in the presence of the compounds mentioned. The polymers obtained feature narrow molecular weight distribution when required, or else, given adjustments to the process, controlled broad or bimodal distribution, and also feature defined end groups. Narrowly distributed polymers based on monomers at least one or all of which contain a diene group (preferably chloroprene) are traditionally not accessible to emulsion polymerization, but in vulcanizate tests feature vulcanizate strengths better than those of broadly distributed polymers of identical average molecular weight. Bimodal polymers generally give better processing than monomodal polymers of identical average molecular weight, in processes involving rubber technology.

DETAILED DESCRIPTION OF THE INVENTION

Compounds of the formula (I)

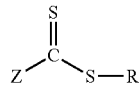
(I)

belong to the dithiocarbamic ester group.

Examples which may be mentioned of the present inventive dithiocarbamic esters of the formula (I) (both the cis form and the trans form are inventive)

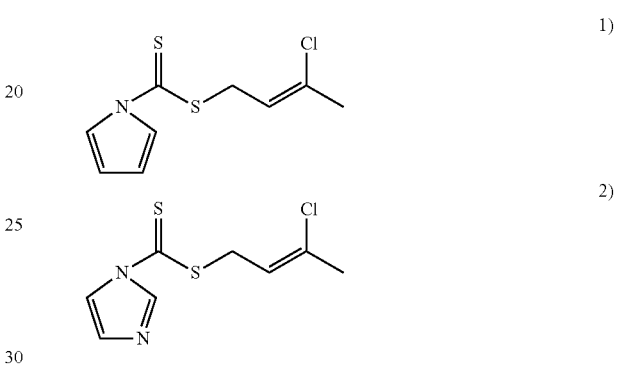

1) 3-chloro-2-butenyl 1H-pyrrole-1-carbodithioate
2) 3-chloro-2-butenyl 1H-imidazole-1-carbodithioate One embodiment of the present inventive process for preparing the compound of formula (I) is characterized in that, in order to avoid side reactions which lead to the formation of strong-smelling by-products and necessitate a subsequent purification stage, the reaction is carried out in the same organic phase, preferably ethers, more preferably tetrahydrofuran, at a temperature of from −78 C. to 80 C., preferably from 0 to 30 C., with no work-up stage or purification stage. The resultant product is obtained pure by evaporating the solvent after removal of the alkali metal halide produced (e.g. potassium hydroxide) by filtration.

In a first step, the carbamic salt Z—C(S)—S-M, M preferably being potassium, is prepared by reacting Z—H with M in an organic phase and then adding carbon disulphide.

The carbamic salt Z—C(S)—S-M is isolated, or, in a preferred form of the process, reacted in-situ with a compound R—X,
where R is preferably

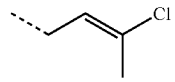

and
X is preferably Cl.

The preferred starting compound R—X, 1,3-dichloro-2-butene, is a known precursor in the industrial synthesis of 2,3-dichlorobutadiene.

The present inventive compounds of formula (I) are suitable for regulating molar mass during the preparation of polychloroprene and polydichlorobutadiene, and copolymers of these. Polychloroprene is used as a rubber in the rubber industry, and also as a raw material for adhesives, and in the form of polychloroprene latices, and also in a blend with crosslinked chloroprene polymers.

In the process for preparing the compound of formula (I), the deprotonation of the amines preferably takes place in aprotic polar organic solvents, or possibly in mixtures of organic solvents with these, preferably in ethers, more preferably in tetrahydrofuran.

According to the present invention, preferred monomers are chloroprene and 2,3-dichlorobutadiene.

The present inventive dithiocarbamic esters feature markedly better regulator activity when compared with traditional molecular weight regulators based on xanthogen disulphide or on mercaptan, and therefore lead to polychloroprene latices with better storage stability. In addition, targeted control of molecular weight is possible via the conversion and via the amount of regulator used, whereas this was not previously possible for emulsion polymers.

2-Chlorobutadiene (chloroprene) can be polymerized in aqueous emulsion in the presence of free-radical initiators. Chloroprene can also be polymerized with various comonomers. Examples of commonly used comonomers include 1-chlorobutadiene, 2,3-dichlorobutadiene, styrene, divenylbenzene, ethyleneglycoldi(meth)acrylate, isoprene, acrylonitrile, acrylates and methacrylates.

For example, addition of 3-chloro-2-butenyl 1H-pyrrole-1-carbodithioate (1), an example of an inventive regulator, can control the molecular weight of the polymer produced in an emulsion polymerization. The polymerization temperature is usually from 5 to 80° C., preferably 10 to 50° C. At these reaction temperatures the polymerization is usually terminated at monomer conversion of from 50 to 90%, preferably from 60 to 80%. Suitable emulsifier systems usually used are alkali metal salts of water-soluble saturated or unsaturated monocarboxylic acids, e.g. (where appropriate disproportionated) resin acids, where appropriate mixed with fatty acids, such as oleic acid or coconut fatty acids. The usual amounts added of the emulsifiers are from 2 to 10 parts by weight (preferably from 3 to 5 parts by weight), based on 100 parts of monomer. Condensation products of naphthalenesulphonic acid and formaldehyde may also be used as additional emulsifiers.

The usual method of initiating and carrying out the polymerization is to add known polymerization initiators. Initiators which may be used are compounds which generate free radicals, e.g. alkali metal persulphates, hydrogen peroxide, and organic peroxides, such as benzoyl peroxide, cumene hydroperoxide, or redox initiators, such as potassium peroxodisulphate/sodium dithionite/sodium sulphite, potassium peroxodisulphate/sodium anthraquinone-2-sulphonate.

Preferably, the polymerization is initiated by adding initiators which decompose thermally at low temperatures, e.g. formamidinesulphinic acid. Inhibitors such as phenothiazine diethylhydroxylamine can terminate the polymerization.

The remaining unconverted monomer may be removed by steam distillation. The pH of the alkaline latex may be lowered to pH 5-7 by dilute acetic acid, and the polymer may be isolated from this emulsion, for example by freeze coagulation, and dried. However, other conventional methods, such as those described in the German patent document DE-A1111804, are also suitable for the work-up process.

For the production of adhesives, the polychloroprene may be dissolved in organic solvents, such as benzene, toluene, methylene chloride or trichloroethylene, or in mixtures of these solvents with other solvents which alone do not dissolve polychloroprene, e.g. petroleum spirit, cyclohexane, or methyl acetate.

The viscosity of the solution depends on the intended use and is preferably from 10 to 100 poise, measured at 20 C. using a Brookfield LVT viscometer.

Other methods of producing polychloroprene adhesives are described in DE-A 12 00 988.

Aliphatic dithiocarbamic esters derived from secondary amines with a pKa value below 12 are generally not suitable as regulators. The products obtained when utilizing these dithiocarbamic esters have very high molecular weights as a consequence of insufficient regulator activity. The use of the present inventive dithiocarbamic esters derived from secondary amines with a pKa of from 12-20, preferably from 14-18, as regulators for the polymerization of chloroprene has not previously been described.

EXAMPLES

Table 1 illustrates the conversion and the amount of regulator, and also the GPC molecular weight of the polychloroprene prepared by the inventive process (see below). Each entry corresponds to the result of an experiment which polymerized chloroprene using a stated combination of regulator and conversion. Clearly, it is only when the present inventive dithiocarbamic esters are used that molecular weight can be controlled simultaneously by way of conversion and amount of regulator, ideally in accordance with the following simple equation known from the living ionic polymerization process.

$$\text{average molecular weight} = (\text{molar amount of monomer} \cdot \text{molecular weight of monomer} \cdot \text{conversion})/(\text{molar amount of regulator}) \quad \text{Equation 1}$$

The Process for the Inventive Preparation of Dithiocarbamic Esters:

To prepare dithiocarbamic esters by the inventive process, 500 ml of THF (anhydrous) and 1 mol of metallic potassium (version A) or liquid NaK alloy (version B) or potassium hydride (version C) formed an initial charge in a 1 L four-necked flask with stirrer, thermometer and dropping funnel, under nitrogen at room temperature. 1 mol of amine compound (dissolved in 150 ml of THF) was added to this charge within 0.5 h. Once the alkali metal had been completely converted to the salt with the amine (visual control), 1 mol of carbon disulphide (dissolved in 240 ml of THF) was added and the mixture was stirred for 1 h. The resultant dithiocarbamate salt was reacted, without prior isolation of the carbamic salt, with 1.5 mol of organic halide compound to give the desired dithiocarbamic ester. The reaction was GC-controlled (GC=gas chromatography) to complete conversion of the dithiocarbamic salt. To separate out the resultant alkali metal halide, the solvent was removed in vacuo and the residue was slurried with 500 mL of pentane. The alkali metal halide was filtered off, and then the solution was concentrated in a 0.1 bar vacuum at 50° C. to give the product with adequate purity. Unconverted organic halide was reclaimed here.

If the same experiments are carried out, but the alkali metal potassium is replaced by sodium (version D) or sodium hydride (version E), this method of conducting the reaction gives a product with severe contamination by-products, requiring the use of advanced purification techniques, such as chromatography, to give the purity needed to produce satisfactory results in the polymerization of chloroprene.

The process used in the Examples herein for the emulsion polymerization of chloroprene: the aqueous phase forming an initial charge in a 3 l glass reactor contained (all parts are parts by weight): 125 parts of deionized water (1 250 g); 2.80 parts of Dresinate 731 in the form of 70% strength solution (40 g); 0.3 part of condensed naphthalenesulphonic acid in the form of 30% strength solution (10 g), 0.65 part of NaOH (6.5 g). To this mixture were added a monomer phase composed of 100 parts of chloroprene (1 000 g) and the desired amount X of parts of regulator (see Table 1). Prior to the start of the polymerization, the reactor was flushed with nitrogen for 1.5 h. The reaction took place under nitrogen. The polymerization time to achieve 60% conversion was from 1-5 h.

Version A: a 2.5% strength solution of formamidinesulphinic acid (FAS) in water was added continuously to initiate the reaction. The reaction temperature was 45 C.

Version B: for redox activation, a 1.5% strength potassium peroxodisulphate solution (PPS) and a 1.0% strength sodium dithionite solution (NHS) in water were added continuously. Reaction temperature 10° C.

At monomer conversion of 60% the reaction was terminated by adding phenothiazine. The remaining monomer was removed from the mixture by steam distillation. After lowering of the pH to 7, the polymer was precipitated using 0.5% strength magnesium chloride solution, and the aqueous phase was filtered off. The product was washed and dried in vacuo overnight at 50° C.

Abbreviations:
Dresinate 731=Na salt of disproportionated resin acid (commercially available from Abieta, for example) (resin acid is a naturally occurring product comparable with tree resin).

Table 1 gives the results of emulsion polymerizations of chloroprene using various regulators in version A of the process: column 1 and 2 shows the components Z and R of the regulator compound. Column 3 gives the used method. The fourth column gives the pKa value of the protonated substituent Z of formula (I). Columns 5 and 6 specify name and structural formulae of the regulator used. Column 7 lists the numbers of the regulator compounds. Column 8 shows the solution viscosity of the resultant polymer at 60%, measured as solution viscosity derived from an 8.6% toluene solution. Column 9 specifies the amount of regulator in mmol added to the mixture, in the monomer phase. Column 10 specifies the number-average molecular weight achieved, measured by GPC. Column 11 differentiates between inventive examples (numerals) and comparative examples (letters).

Except regulator compound (7) all comparative compounds have been derived by Method A! In case of regulator compounds 8-11 an alcohol has been used (isopropylalcohol) instead of an amine (pyrrol/imidazol).

TABLE 1

| Z | R | Version | pKa value Z-H | IUPAC name | Formula | Regulator compound | Solution viscosity/ mPas (LVL) | Parts of regulator | $M_n$ | Inventive/comparative examples |
|---|---|---|---|---|---|---|---|---|---|---|
| 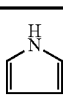 | 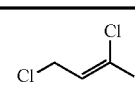 | A | 17.0 | 3-Chloro-2-butenyl 1H-pyrrole-1-carbodithioate (1) | 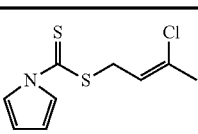 | (1) | 14 | 15 mmol | 50000 | 1 |
|  | 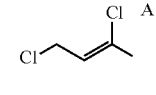 | A | 14.5 | 3-Chloro-2-butenyl 1H-imidazole-1-carbodithioate (2) | 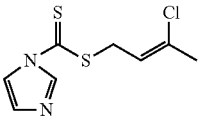 | (2) | 35 | 15 mmol | 101000 | 2 |
| 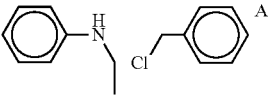 | 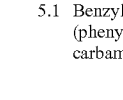 | A | 5.1 | Benzyl ethyl-(phenyl)dithio-carbamate (3) | 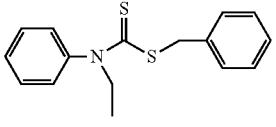 | (3) | gelled | 15 mmol | | A |
| 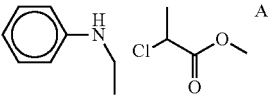 | 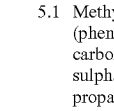 | A | 5.1 | Methyl 2-({[ethyl-(phenyl)amino]-carbonothioyl}-sulphanyl)-propanoate (4) | 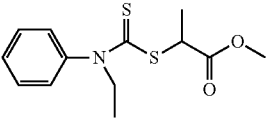 | (4) | gelled | 15 mmol | | B |
| 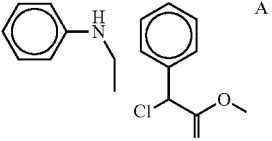 | 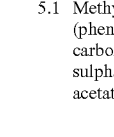 | A | 5.1 | Methyl ({[ethyl-(phenyl)amino]-carbonothioyl}-sulphanyl)(phenyl) acetate (5) | 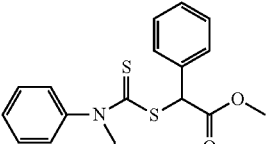 | (5) | gelled | 15 mmol | | C |
| 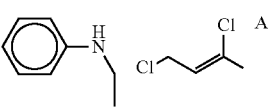 | 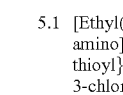 | A | 5.1 | [Ethyl(phenyl)-amino]carbono-thioyl}sulphanyl-3-chloro-2-butenyl (6) | 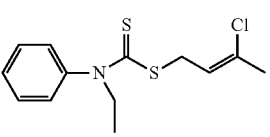 | (6) | gelled | 15 mmol | | D |

TABLE 1-continued

| Z | R | Version | pKa value Z-H | IUPAC name | Formula | Regulator compound | Solution viscosity/ mPas (LVL) | Parts of regulator | $M_n$ | Inventive/comparative examples |
|---|---|---|---|---|---|---|---|---|---|---|
| DE-A 30 44811 | | A | | Methylenetrimethylolpropane-xanthogen disulphide (7) | | (7) | 67 | 15 mmol | 168000 | E |
| (isopropyl)-OH | Cl-CH2-phenyl | A | | S-Benzyl O-isopropyldithiocarbonate (8) | | (8) | gelled | 15 mmol | | F |
| (isopropyl)-OH | CH3-CHCl-C(O)-O-CH3 | A | | Methyl 2-[(isopropoxycarbonothioyl)-sulphanyl]-propanoate (9) | | (9) | gelled | 15 mmol | | G |
| (isopropyl)-OH | phenyl-CHCl-C(O)-O-CH3 | A | | Methyl [(isopropoxycarbonothioyl)sulphanyl]-(phenyl)acetate (10) | | (10) | gelled | 15 mmol | | H |
| (isopropyl)-OH | Cl-CH2-C(Cl)=CH-CH3 | A | | [(Isopropoxycarbonothioyl)-sulphanyl]-3-chloro-2-butenyl (11) | | (11) | gelled | 15 mmol | | I |

Table 2 includes experiments to investigate molecular weight as a function of conversion and ratio of amount of monomer to amount of regulator. A comparison is made of the results of emulsion polymerization of chloroprene using a xanthogen disulphide regulator (regulator compound (7) see Table 1 and DE-A 304 48 11) and using the inventive dithiocarbamic ester (regulator compound (1) see Table 1) prepared by the inventive process and polymerized by version A. Column 1 lists the regulator compound used. Column 2 includes the amount of regulator used. Column 3 contains the conversions, and column 4 contains the theoretical molecular weights calculated from these data by Equation 1. Columns 5 and 6 include the molecular weights determined experimentally by GPC and the polydispersity index of the polymer calculated as the quotient derived from the weight average and the number average from GPC. The polymerizations were conducted to a conversion of 60%. Column 7 differentiates between inventive examples (numerals) and comparative examples (letters).

TABLE 2

| Regulator compound | Parts of regulator | Conversion/% | Mn theor. | Mn (GPC) | Mw/Mn | Example/ Comp. Ex. |
|---|---|---|---|---|---|---|
| (1) | 0.35 | 19 | 13 000 | 14 000 | 2.4 | 3 |
| | | 43 | 29 000 | 36 000 | 1.5 | |
| | | 60 | 40 000 | 49 000 | 1.5 | |
| (1) | 0.233 | 21 | 21 000 | 33 500 | 1.7 | 4 |
| | | 41 | 41 000 | 53 600 | 1.7 | |
| | | 61 | 61 000 | 72 800 | 2.5 | |
| (1) | 0.116 | 20 | 40 000 | 56 500 | 1.6 | 5 |
| | | 39 | 78 000 | 84 600 | 1.6 | |
| | | 60 | 120 000 | 131 800 | 1.8 | |
| (1) | 0.075 | 25 | 78 000 | 102 000 | 1.8 | 6 |
| | | 41 | 127 000 | 127 000 | 1.8 | |
| | | 61 | 190 000 | 190 000 | 2.3 | |

TABLE 2-continued

| Regulator compound | Parts of regulator | Conversion/% | Mn theor. | Mn (GPC) | Mw/Mn | Example/ Comp. Ex. |
|---|---|---|---|---|---|---|
| (7) | 0.75 | 20 | 34 000 | 148 700 | 2.1 | J |
|  |  | 40 | 34 000 | 142 000 | 2.3 |  |
|  |  | 60 | 34 000 | 148 700 | 2.6 |  |

Mn = number-average molecular weight
Mw = weight-average molecular weight
GPC = gel permeation chromatography Table 3 shows further results of polymerizations by the process described, versions A and B. Suitable dithiocarbamic ester regulators from Table 1 are compared in the emulsion polymerization of chloroprene. Column 1 lists the regulator compound used. Column 2 describes the process version used. Column 3 includes the amount of regulator used and the theoretical molecular weights calculated from these data by Equation 1. Columns 4 and 5 include the molecular weights determined experimentally by GPC and the polydispersity index of the polymer calculated as the quotient derived from the weight average and the number average from GPC. The polymerizations were conducted to a conversion of 60%.

TABLE 3

| Regulator compound | Version | Pts. of regulator/ $M_n$ (calc.) | $M_n$ (GPC) | Mw/Mn | Example |
|---|---|---|---|---|---|
| (1) | A | 0.35 pts./40 000 | 49 000 | 1.5 | 7 |
| (1) | A | 0.116 pts./120 000 | 130 000 | 1.8 | 8 |
| (1) | B | 0.116 pts./120 000 | 104 000 | 1.7 | 9 |
| (2) | A | 0.233 pts./60 000 | 115 000 | 2.0 | 10 |
| (1) | A* | 0.233 pts./60 000 | 74 000 | 1.6 | 11 |
| (1) | A** | 0.233 pts./60 000 | —*** | — | 12 |

*Monomer used: 94 parts (pts.) of chloroprene and 6 parts of 2,3-dichlorobutadiene
**Monomer: 2,3-dichlorobutadiene
***GPC measurement not possible; viscosity measurements on conversion samples show rise in molecular weight As illustrated in the previous Examples and Tables 1-3 the known xanthogen esters tested are unsuitable as regulators for the polymerization of chloroprene under the desired conditions. However, dithiocarbamic esters based on secondary amines with a pKa of the protonated form from 12 to 20, preferably from 14-18, exhibit regulator activity in the emulsion polymerization of chloroprene and 2,3-dichlorobutadiene and the activity is markedly higher than for the known regulators based on xanthogen disulphides (DE-A 304 48 11).

Inventive compounds (1) and (2) have preferred features and as illustrated in Example 1, the compounds gives good agreement between conversion and molecular weight. As illustrated in the previous Examples, activity of the inventive regulators is very good over the entire temperature range relevant to the emulsion polymerization of chloroprene, from 5 to 80° C., preferably from 10 to 45° C., and in combination with all of the initiator systems commonly used for emulsion polymerization of chloroprene.

The polymerization time needed to achieve a conversion of 60%, from 1 to 5 hours, which ensures that heat can be dissipated, even during large-scale industrial production.

Table 4 lists the results of the experiments in the preparation of suitable dithiocarbamic esters for the controlled polymerization of chloroprene. Column 1 includes the process version used. Columns 2 and 3 show the components Z and R of the regulator compound. Column 4 lists the yield of regulator substance in %. Column 5 differentiates between inventive examples (numerals) and comparative examples (letters).

TABLE 4

| Version | Amine (Z) | Organic halide (R-X) | Yield | Inventive/ comparative examples | See Table 1 Inventive |
|---|---|---|---|---|---|
| A | Pyrrole | 1,3 Dichloro-2-butene | 81.5% | 13 | (1) |
| A | Imidazole | 1,3 Dichloro-2-butene | 80.6% | 14 | (2) |
| B | Pyrrole | 1,3 Dichloro-2-butene | 78.5% | 15 | (1) |
| C | Pyrrole | 1,3 Dichloro-2-butene | 65% | 16 | (1) |
| D | Pyrrole | 1,3 Dichloro-2-butene | 72%* | K | (1) |
| E | Pyrrole | 1,3 Dichloro-2-butene | 78%* | L | (1) |

*Product purity about 80%

Comparative Examples (in Accordance with WO 99/31144)

M: Synthesis of benzyl 1-pyrrolecarbodithioate

Pyrrole (1.34 g, 20 mmol) was added dropwise, with stirring, to a suspension of sodium hydride (0.48 g, 20 mmol) in dimethyl sulphoxide (20 mL). Once the addition has ended, the resultant brown suspension was stirred for a further 30 min at room temperature before adding carbon disulphide (1.52 g, 20 mmol). The solution was stirred for a further 30 min at room temperature, and finally the benzyl chloride (2.53 g, 20 mmol) was added. After 1 h, water (20 mL) was added to the reaction mixture, followed by diethyl ether (20 mL). The organic phase was separated off, and then the aqueous phase was extracted twice, each time with 20 mL of diethyl ether. The combined organic phases were dried, using magnesium sulphate, and filtered, and the solvent was distilled off. The crude product was separated chromatographically, using 5% strength ethyl acetate in petroleum ether. The pure product was isolated in the form of a yellow oil at 50% yield (2.34 g).

N: Synthesis of benzyl 1-imidazolecarbodithioate:

Benzyl mercaptan (0.68 g, 5 mmol) was added dropwise at room temperature to a solution of thiocarbonyldiimidazole (0.89 g, 5.5 mmol) in dichloromethane (10 mL). The solution was stirred for 30 min at the same temperature, and finally the solvent was removed in vacuo. The residue was separated chromatographically (silica gel 60, 70-230 mesh), using a solvent mixture composed of ethyl acetate and petroleum ether in a ratio of 3:7 as eluent. The product isolated was benzyl 1-imidazolecarbo-dithioate (65) in the form of a pale yellow solid at 54% yield (0.78 g).

When direct comparison is made of the process of the invention with processes known from the literature and cited above, the inventive process has marked advantages in product yield, and also in particular in the omission of complicated purification steps which reduce yield.

Inventive regulators prepared by this process can control molecular weight and microstructure (copolymer composition, end groups) in the emulsion polymerization of chloroprene and 2,3-dichlorobutadiene, and also in the copolymerization of chloroprene and 2,3-dichlorobutadiene with vinyl monomers and with diene monomers.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A polymer which contains end groups of the formula (VI)

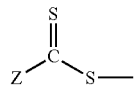

(VI)

and end groups of the formula (VIa)
R— (VIa),
R is a halogen-substituted alkenyl radical, and where
Z is either a substituted or unsubstituted heterocyclic radical which contains at least one nitrogen atom and which has linkage at one nitrogen atom to the —CS$_2$—R group of formula (VI) and which, in the parent form in which there is a hydrogen atom bonded to the nitrogen atom which has linkage to the —CS$_2$R group of formula (VI), has a pK$_a$ value in the range from 12 to 20, or where
Z is a radical of the formula (II),

(II)

where
A and B have been selected independently of one another from the group consisting of hydrogen, substituted or unsubstituted alkyl, substituted or unsubstituted alkenyl, substituted or unsubstituted alkoxy, substituted or unsubstituted acyl, substituted or unsubstituted aroyl, substituted or unsubstituted aryl, substituted or unsubstituted heteroaryl, substituted or unsubstituted alkylsulphonyl, substituted or unsubstituted alkylsulphinyl, substituted or unsubstituted alkylphosphonyl, substituted or unsubstituted arylsulphinyl and substituted or unsubstituted arylphosphonyl, and where the pK$_a$ value of the protonated form of formula (III)

(III)

is in the range from 12 to 20.

2. The polymer according to claim 1, where the polymer is polychloroprene poly-2,3-dichlorobutadiene or polychloroprene-co-2,3-dichlorobutadiene.

* * * * *